(12) United States Patent
Ching

(10) Patent No.: US 11,541,146 B2
(45) Date of Patent: Jan. 3, 2023

(54) METHOD AND DEVICE FOR CAPTURING AND DISINFECTING CONTAMINANTS FOR DRAINAGE SYSTEM

(71) Applicant: Wing Han Ching, Hong Kong (HK)

(72) Inventor: Wing Han Ching, Hong Kong (HK)

(73) Assignee: Wing Han Ching, Hong Kong (HK)

( * ) Notice: Subject to any disclaimer, the term of this patent is extended or adjusted under 35 U.S.C. 154(b) by 0 days.

(21) Appl. No.: 17/528,216

(22) Filed: Nov. 17, 2021

(65) Prior Publication Data

US 2022/0249730 A1    Aug. 11, 2022

(30) Foreign Application Priority Data

Feb. 7, 2021   (CN) .......................... 202110174867.9

(51) Int. Cl.
*A61L 9/20*          (2006.01)
(52) U.S. Cl.
CPC ........... *A61L 9/205* (2013.01); *A61L 2209/12* (2013.01); *A61L 2209/15* (2013.01)
(58) Field of Classification Search
CPC ... A61L 9/205; A61L 2209/12; A61L 2209/15
See application file for complete search history.

(56) References Cited

U.S. PATENT DOCUMENTS

| 5,997,733 A * | 12/1999 | Wilbur ................... A61L 11/00 210/85 |
| 10,786,592 B2 * | 9/2020 | Keith ................... B01D 53/885 |
| 2017/0080373 A1 * | 3/2017 | Engelhard ............ B01D 46/448 |

FOREIGN PATENT DOCUMENTS

| CN | 202466793 U | 10/2012 |
| CN | 105999352 A | 10/2016 |
| CN | 210984221 U | 7/2020 |
| CN | 211499038 U | 9/2020 |
| DE | 102005036580 A1 | 3/2007 |

\* cited by examiner

*Primary Examiner* — Sean E Conley
*Assistant Examiner* — Brendan A Hensel
(74) *Attorney, Agent, or Firm* — Idea Intellectual Limited; Margaret A. Burke; Sam T. Yip

(57) ABSTRACT

Provided herein is a disinfection device for drainage system comprising: a housing comprising a chamber and a top end, the chamber having a body and a reducing part, the reducing part including a first opening at the bottom end of the chamber and a floating body configured to seal the first opening at the bottom end; a spiral guiding channel having an inlet and an outlet, the spiral guiding channel connected to the chamber through the outlet; an exhaust conduit having an expandable part at one end of the exhaust conduit, the exhaust conduit connecting to the top end of the housing and partially extending through the body of the chamber; and a disinfection part equipped in the interior of the disinfection device so as to remove air contaminants when air passing through the chamber from the spiral guiding channel to the exhaust conduit.

16 Claims, 2 Drawing Sheets

METHOD AND DEVICE FOR CAPTURING AND DISINFECTING CONTAMINANTS FOR DRAINAGE SYSTEM

CROSS-REFERENCE TO RELATED APPLICATIONS

The present application claims priority from a Chinese patent application No. 202110174867.9 filed Feb. 7, 2021, and the disclosure of which is incorporated herein by reference in its entirety.

FIELD OF THE INVENTION

The present invention provides a disinfection device and method for disinfecting contaminants for the drainage system. More specifically, the disinfection device is able to capture and disinfect the contaminants of the exhaust air when the exhaust air passing through the chamber of the disinfection device from the spiral guiding channel to the exhaust conduit or vice versa.

BACKGROUND

Usually, the waste, excreta and dirty water produced from each house is discharged by the drainage system. More specifically, the drainage system includes branch pipes and main vertical drainage pipes, where the branch pipes are configured to collect the waste from sanitary fitments in each flat of each floor, then followed by gathering to the main drainage pipes. When infectious pollutants are discharged from one of the houses, the infectious aerosols thereof will be released and spread to the nearby resident from the opening of drainage pipes located at roof of building through the interconnected drainage pipes, resulting in the impact on the lives of nearby residents.

The outbreak of SARS in Amoy Gardens in 2003 and similar transmission route of COVID-19 at Fu Heng Estate in 2020 were all related to the design of the existing drainage system. Specifically, in regard to the incident at Fu Heng Estate, a resident of unit 13 on the 32nd floor was earlier confirmed to be infected with COVID-19. The drainage pipe of unit 13 terminated at the roof of the building and was located opposite to unit 14. Infected aerosol was suspected to have discharged from the open end of the drainage pipe at the roof of the building and transmitted to unit 14 on the $34^{th}$ floor, the top floor of the building, by wind wake effect.

In view of the disadvantages of the existing drainage system, there is a need for providing a disinfection device and method adaptable to the drainage system so as to eliminate or reduce the potential transmission of infected aerosol or contaminants from the open end of the drainage pipe.

SUMMARY OF THE INVENTION

Accordingly, a first aspect of the present invention provides a disinfection device for drainage system. The disinfection device includes a housing having a chamber and at least a top end, a spiral guiding channel having an inlet and an outlet, an exhaust conduit having an expandable part at one end of the exhaust conduit and a disinfection part equipped in the interior of the disinfection device. The chamber includes a body and a reducing part and the spiral guiding channel is adjacent to the exterior wall of the housing and connected to the chamber through the outlet. Further, the exhaust conduit positioned in the chamber connected to the top end of the housing and partially extends through the body of the chamber. Therefore, the configuration of the spiral guiding channel, chamber, and the exhaust conduit would not block the air pathway, and the air flow in and out freely to the drainage system. Moreover, the disinfection part is configured to remove air contaminants from air passing through the chamber from the spiral guiding channel to the exhaust conduit.

In one embodiment of the first aspect of the present invention, there is provided a disinfection device where the housing further includes a cover positioned on the top end of the housing.

In one embodiment of the first aspect of the present invention, there is provided a disinfection device where the expandable part includes a top opening and a bottom opening; wherein the cross-sectional area of the bottom opening is larger than the cross-sectional area of the top opening.

In one embodiment of the first aspect of the present invention, there is provided a disinfection device where the cross-sectional area of the exhaust conduit is equal to or slightly smaller than the cross-sectional area of the top opening of the expandable part.

In one embodiment of the first aspect of the present invention, there is provided a disinfection device where the disinfection part comprises a photocatalyst layer positioned on the interior wall of the body and at least one ultraviolet lamp positioned on the exterior wall of the exhaust conduit.

In one embodiment of the first aspect of the present invention, there is provided a disinfection device where the spiral guiding channel is set along the tangent plane of the housing.

In one embodiment of the first aspect of the present invention, there is provided a disinfection device where the cross-sectional area of the spiral guiding channel is continuously reduced from the inlet of the spiral guiding channel to the outlet of the spiral guiding channel so as to spin the air before entering into the chamber.

In one embodiment of the first aspect of the present invention, there is provided a disinfection device where the housing further comprises a clamping part extended from the housing so as to mount the disinfection device on the drainage system.

In one embodiment of the first aspect of the present invention, there is provided a disinfection device where the reducing part includes a first opening at the bottom end of the chamber and a floating body configured to seal the first opening at the bottom end.

In one embodiment of the first aspect of the present invention, there is provided a disinfection device where the size of the floating body is greater than the aperture of the first opening of the bottom.

In one embodiment of the first aspect of the present invention, there is provided a disinfection device where the density of the floating body is smaller than the density of the water.

In one embodiment of the first aspect of the present invention, there is provided a disinfection device where air from atmosphere enter from the top end of the housing, followed by the exhaust conduit and the spiral guiding channel when the drainage system in negative pressure.

A second aspect of the present invention provides a method for removing contaminants from exhaust air of a drainage system, which includes (1) providing exhaust air having contaminants through a spiral guiding channel to a disinfection device having a chamber including a body, a reducing part and a disinfection part; (2) disinfecting the exhaust air by the disinfection part including a photocatalyst layer positioned on the interior wall of the chamber and at least one ultraviolet lamp positioned on the exterior wall of the exhaust conduit to obtain a sterile air; (3) discharging the sterile air through the exhaust conduit. More specifically, the spiral guiding channel is connected to the chamber such that the exhaust air flow from the spiral guiding channel to the chamber and the contaminants are captured and removed by the disinfection part of the chamber.

A third aspect of the present invention provides a method for removing contaminants from mixture of water and exhaust air of a drainage system, which includes (1) providing the mixture having the water and the exhaust air having contaminants through an exhaust conduit to a disinfection device having a chamber including a body, a reducing part and a disinfection part; (2) disinfecting the exhaust air by the disinfection part; (3) discharging the sterile air through a spiral guiding channel; (4) accumulating the water at the reducing part including a first opening at the bottom end of the chamber and a floating body configured to seal the first opening at the bottom end of the chamber; (5) discharging the water through the first opening at the bottom end of the chamber to the drainage system. More specifically, the exhaust conduit connects and extends into the disinfection device and the disinfection part further includes a photocatalyst layer positioned on the interior wall of the chamber and at least one ultraviolet lamp positioned on the exterior wall of the exhaust conduit so as to disinfect the contaminants of the exhaust air. Moreover, the water would be accumulated at the bottom end of the chamber due to the block of the floating body, and once the buoyancy is greater than the weight of the floating body, the water is discharged through the first opening at the bottom end of the chamber.

BRIEF DESCRIPTION OF THE DRAWINGS

The appended drawings, where like reference numerals refer to identical or functionally similar elements, contain figures of certain embodiments to further illustrate and clarify the above and other aspects, advantages and features of the present invention. It will be appreciated that these drawings depict embodiments of the invention and are not intended to limit its scope. The invention will be described and explained with additional specificity and detail through the use of the accompanying drawings in which.

Definitions

Figure 1:
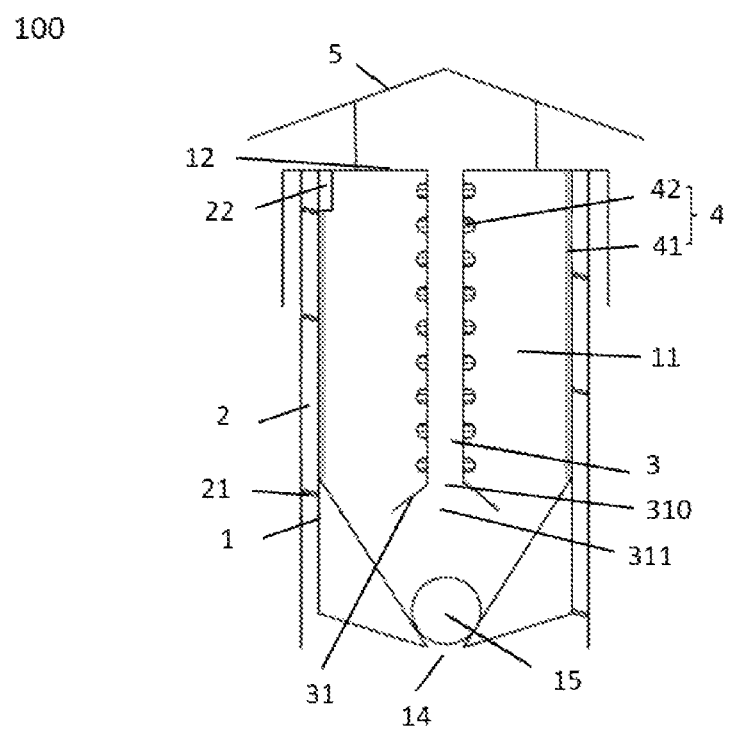
FIG. 1 depicts a side cross-sectional view of the disinfection device in one embodiment of the present invention.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

DETAILED DESCRIPTION

In the following description, the present disinfection devices are set forth as preferred examples. It will be apparent to those skilled in the art that modifications, including additions and/or substitutions may be made without departing from the scope and the spirit of the invention. Specific details may be omitted so as not to obscure the invention; however, the disclosure is written to enable one skilled in the art to practice the teachings herein without undue experimentation.

The present invention provides a disinfection device which is able to remove contaminants or infected aerosol from the exhaust air in order to sterilize thereof. More specifically, the disinfection device includes a housing having a chamber and at least a top end, a spiral guiding channel having an inlet and an outlet, an exhaust conduit having an expandable part at one end of the exhaust conduit and a disinfection part equipped in the interior of the disinfection device. The spiral guiding channel is adjacent to the exterior wall of the housing and connected to the chamber through the outlet. In addition, the disinfection device further includes a clamping part such that the disinfection device in the present invention is able to be mounted at the edge of an opening of the draining pipe. The spiral guiding channel is connected to the chamber and is utilized to accelerate the flow of the exhaust air before entering into the chamber when the drainage system is in positive pressure. Due to the cyclonic effect, the relatively heavier infected aerosol or contaminants will land on the inner surface of the chamber and be disinfected or sterilized by the disinfection part equipped with a photocatalyst layer when the photocatalyst is activated. Then, the disinfected air will be discharged to the atmosphere through the exhaust conduit connecting to the top end of the housing.

The chamber further includes a body and a reducing part, where the reducing part includes a first opening at the bottom end of the chamber and a floating body configured to seal the first opening at said bottom end. When the drainage system is in negative pressure, the air from the atmosphere enters into the drainage system along a pressure gradient through the disinfection device in the present invention. In case where there is rainwater entering into the disinfection device and accumulating at the reducing part of the chamber of the disinfection device, the floating body will float up and allow the water to be discharged to the drainage system once the buoyancy of the floating body is over the weight thereof. Once the water is discharged, the floating body will return to its initial position and seal the first opening at the bottom end of the chamber so as to stop the infected aerosol bypassing the body of the chamber and releasing to the atmosphere.

Figure 2:
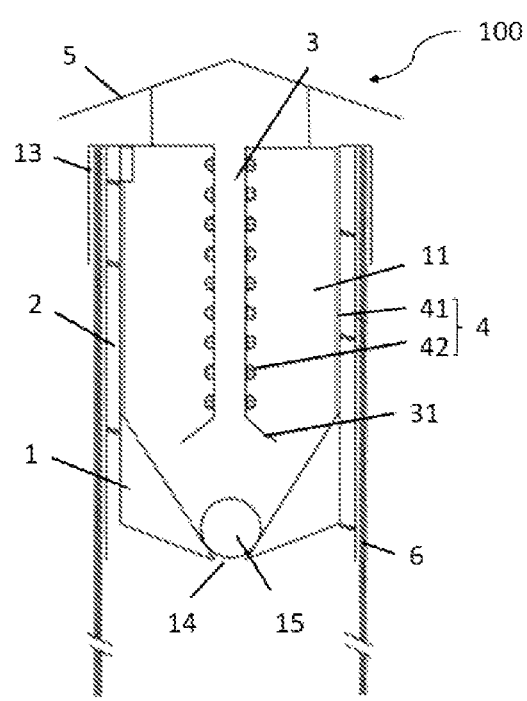
FIG. 2 depicts the disinfection device of one embodiment of the present invention being installed to a typical drainage pipe.

FIG. 1 illustrates a cross-sectional view of the capture and disinfected device 100 in one embodiment of the present invention (hereinafter as "the device"). The device 100 includes a housing 1 having a chamber 11 and a top end 12, a spiral guiding channel 2 having an inlet 21 and an outlet 22, an exhaust conduit 3 having an expandable part 31 at one end of the exhaust conduit and a disinfection part 4 equipped in an interior of the device 100. The spiral guiding channel 2 is adjacent to an exterior wall of the housing 1 and connected to the chamber 11 through the outlet 22. In one embodiment of the present invention, the housing 1 further includes a clamping part 13 to mount the device 100 on the drainage pipe 6 of the drainage system as shown in FIG. 2. In another embodiment of the present invention, the clamping part 13 is further provided with a groove where an opening of the groove is facing downward of the housing 1. The opening of the groove can be clamped on an interior wall of the drainage pipe 6 to make the housing 1 stay more steadily on the drainage system. Preferably, to avoid gas leakage, the groove further includes a sealing gasket between the housing 1 and the interior wall of the drainage pipe 6. The clamping part 13 is detachable from the drainage pipe 6.

When the drainage system is in positive pressure, the exhaust air with infected aerosol or contaminants flows into the device 100 from the inlet 21 of the spiral guiding channel to the chamber 11. Before entering into the chamber 11, the exhaust air will be accelerated and span several times by the spiral guiding channel 2. Due to the cyclonic effect, the relatively heavier infected aerosol and contaminants will land on the inner surface of the chamber 11. Preferably, the cross-sectional area of the spiral guiding channel 2 decreases from the inlet 21 to the outlet 22 so as to increase the flow speed of the exhaust air when flowing through the spiral guiding channel 2 and entering into the chamber 11. The increase in the flow speed of the exhaust air will enforce the centrifugal force to the infected aerosol or contaminants in the exhaust air, such that the infected aerosol or contaminants can more easily adhere to the inner surface of the chamber 11. Preferably, the housing 1 is in a cylindrical shape and the outlet 22 of the spiral guiding channel 2 is set along the tangent plane of the housing 1, such that the gas is able to perform a circular movement along the inner surface of the chamber 11 to improve the adhesion effect of aerosol in the gas.

In one embodiment of the present invention, the disinfection part 4 and the exhaust conduit 3 further include a photocatalyst layer 41 and ultraviolet lamps 42, respectively. The photocatalyst layer 41 produces active oxygen under the activation by, for example, but not limited to the ultraviolet light emitted from ultraviolet lamps 42 or other visible light, which oxidizes and decomposes the infected aerosol adsorbed on the inner surface of the chamber 11 into substances such as carbon dioxide and water to effectively reduce the emission of infectious aerosol and contaminants.

In another embodiment of the present invention, the expandable part 31 of the exhaust conduit 3 includes a top opening 310 and a bottom opening 311 wherein the cross-sectional area of the bottom opening 311 is larger than the cross-sectional area of the top opening 310. The expandable part 31 can reduce the speed of the air flow in the chamber 11 so as to avoid the adsorbed aerosol on the inner surface of the chamber 11 being dissolved and aerosolized again and then discharged into the atmosphere through the exhaust conduit 3. Moreover, the expandable part 31 can also effectively block the light emitted from the ultraviolet lamps 42 to prevent creatures such as insects from being attracted by the light leading to entry into the interior of the chamber 11.

When the drainage system is in negative pressure, air from the atmosphere flows into the drainage pipe 6 through the device 100 of the present invention along a pressure gradient. More specifically, the air will flow from the exhaust conduit 3 into the chamber 11, then to the drainage pipe 6 through the spiral guiding channel 2 as shown in FIG. 2. Meanwhile, the air is also disinfected or sterilized when flowing through the disinfection part 4 in the chamber 11 so as to keep the incoming air to the drainage system disinfected.

In another embodiment of the present invention, the device 100 further includes a cover 5 positioned on the top end 12 of the housing to reduce the water entering into the device 100 directly. The water initially accumulates at the bottom end of the chamber due to the blockage of the floating body 15. When the water reaches a level that the water density is higher than that of the floating body 15, the floating body 15 will float and the opening 14 will be unblocked, such that the accumulated water is discharged to the drainage pipe 6 through the opening 14 at the bottom end of the chamber. After the discharge of the water, the floating body 15 will return to the original position to block the opening 14 at the bottom end of the chamber so as to avoid the gas from the drainage pipe 6 bypassing into the chamber 11. Preferably, the structure of the bottom of the chamber is formed as a reducing part, but not limited to a reverse conical structure so as to improve the water collection efficiency.

The present invention also provides a method for removing contaminants from the exhaust air of a drainage system, which includes following steps: (1) the exhaust air having contaminants flows through the spiral guiding channel 2 into the device 100; (2) the contaminants of the exhaust air are absorbed on the inner surface of the chamber 11 due to the centrifugal force and then disinfected by the disinfection part 4 equipped on the inner surface of the chamber 11 to obtain a sterile air; (3) the sterile air is discharged to the atmosphere through the exhaust conduit 3. Moreover, the present invention provides another method for removing contaminants from mixture of water and exhaust air of a drainage system, which includes following steps: (1) the mixture of the water and the exhaust air having contaminants flow through the exhaust conduit 3 into the device 100; (2) the contaminants of the exhaust air are absorbed on the inner surface of the chamber 11 and then disinfected by the disinfection part 4 equipped on the inner surface of the chamber 11 to obtain a sterile air; (3) the sterile air is discharged to the drainage pipe 6 through the spiral guiding channel 2; (4) the water accumulates at the bottom end of the chamber 11 where a floating body 15 is configured to block the opening 14 at the bottom end of the chamber; (5) the water is discharged through the opening 14 at the bottom end of the chamber 11 to the drainage pipe 6. The aforementioned methods can significantly reduce or eliminate the emission of infectious aerosol in the main drainage pipe so as to avoid the impact of the infectious aerosol on the environment and reduce the impact on the lives of surrounding residents.

Although the invention has been described in terms of certain embodiments, other embodiments apparent to those of ordinary skill in the art are also within the scope of this invention. Accordingly, the scope of the invention is intended to be defined only by the claims which follow.

The invention claimed is:

1. A disinfection device for a drainage system, comprising:
   a housing comprising a chamber and a top end, the chamber having a body and a reducing part, wherein the reducing part comprises an opening at a bottom end of the chamber and a floating body configured to seal the opening at the bottom end;
   a spiral guiding channel being external to the chamber and having an inlet and an outlet, the spiral guiding channel being adjacent to an exterior wall of the housing and connected to the chamber through the outlet;
   an exhaust conduit having an expandable part at one end of the exhaust conduit, the exhaust conduit positioned in the chamber, connecting to the top end of the housing and partially extending through the body of the chamber, wherein the exhaust conduit is partially defined by an interior wall of the body, and the expandable part is positioned in the chamber; and
   a disinfection part installed in an interior of the disinfection device, so as to remove air contaminants when air passing through the chamber from the spiral guiding channel to the exhaust conduit.

2. The disinfection device of claim 1, wherein the housing further comprises a cover positioned on the top end of the housing.

3. The disinfection device of claim 1, wherein the expandable part comprises a top opening and a bottom opening, and wherein a cross-sectional area of the bottom opening is larger than a cross-sectional area of the top opening.

4. The disinfection device of claim 3, wherein a cross-sectional area of the exhaust conduit is equal to or slightly smaller than the cross-sectional area of the top opening of the expandable part.

5. The disinfection device of claim 1, wherein the disinfection part further comprises a photocatalyst layer positioned on the interior wall of the body and at least one ultraviolet lamp positioned on an the exterior wall of the exhaust conduit.

6. The disinfection device of claim 1, wherein the spiral guiding channel is set along a tangent plane of the housing.

7. The disinfection device of claim 1, wherein the cross-sectional area of the spiral guiding channel is continuously reduced from the inlet of the spiral guiding channel to the outlet of the spiral guiding channel so as to spin the air before entering into the chamber.

8. The disinfection device of claim 1, wherein the housing further comprises a clamping part extended from the housing so as to mount the disinfection device on the drainage system.

9. The disinfection device of claim 1, wherein the size of the floating body is greater than the aperture of the opening of the bottom.

10. The disinfection device of claim 1, wherein the density of the floating body is smaller than the density of the water.

11. A method for removing contaminants from exhaust air of a drainage system using the disinfection device of claim 1, the method comprising:
    providing exhaust air having contaminants through the spiral guiding channel of the disinfection device to the chamber of the disinfection device;
    disinfecting the exhaust air by the disinfection part of the disinfection device, the disinfection part including a photocatalyst layer positioned on an interior wall of the chamber and at least one ultraviolet lamp positioned on an exterior wall of the exhaust conduit positioned in the chamber to obtain a sterile air; and
    discharging the sterile air through the exhaust conduit.

12. A method for removing contaminants from mixture of water and exhaust air of a drainage system using the disinfection device of claim 1, the method comprising:
    providing the mixture having the water and the exhaust air having contaminants through the exhaust conduit of the disinfection device, the exhaust conduit connecting and extending into the chamber of the disinfection device;
    disinfecting the exhaust air by the disinfection part of the disinfection device, the disinfection part including a photocatalyst layer positioned on an interior wall of the chamber and at least one ultraviolet lamp positioned on an exterior wall of the exhaust conduit to obtain a sterile air;
    discharging the sterile air through the spiral guiding channel of the disinfection device;
    accumulating the water at the reducing part of the disinfection device, the disinfection part including an opening at the bottom end of the chamber and a floating body configured to seal an opening at an bottom end of the chamber; and
    discharging the water through the opening at the bottom end of the chamber to the drainage system.

13. The disinfection device of claim 1, wherein the reducing part is located directly under the exhaust conduit, wherein, along a direction from the exhaust conduit toward the reducing part, a cross-sectional area of the expandable part is increased along the direction, and a cross-sectional area of the reducing part is decreased along the direction.

14. The disinfection device of claim 1, wherein at least one chamber channel of the chamber is collectively defined by the interior wall of the body and an exterior wall of the exhaust conduit, and the chamber channel is adjacent to the exhaust conduit.

15. The disinfection device of claim 14, wherein the chamber channel communicates with the spiral guiding channel through the outlet of the spiral guiding channel, wherein the spiral guiding channel makes a turn adjacent to the top end of the housing, such that a flowing direction of air in the spiral guiding channel is opposite to a flowing direction of air in the chamber channel.

16. The disinfection device of claim 14, wherein the at least one chamber channel of the chamber further comprises a first chamber channel and a second chamber channel, wherein the first and second chamber channels are located two opposite sides of the exhaust conduit.

* * * * *